United States Patent
Harder et al.

(10) Patent No.: US 11,246,660 B2
(45) Date of Patent: Feb. 15, 2022

(54) SIMULATING BREAST DEFORMATION (71) Applicant: KONINKLIJKE PHILIPS N.V., Eindhoven (NL)

(72) Inventors: Tim Philipp Harder, Ahrensburg (DE); Thomas Buelow, Grosshansdorf (DE)

(73) Assignee: Koninklijke Philips N.V., Eindhoven (NL)

( * ) Notice: Subject to any disclaimer, the term of this patent is extended or adjusted under 35 U.S.C. 154(b) by 988 days.

(21) Appl. No.: 15/749,272

(22) PCT Filed: Aug. 16, 2016

(86) PCT No.: PCT/EP2016/069426
§ 371 (c)(1),
(2) Date: Jan. 31, 2018

(87) PCT Pub. No.: WO2017/029288
PCT Pub. Date: Feb. 23, 2017

(65) Prior Publication Data
US 2018/0221092 A1  Aug. 9, 2018

(30) Foreign Application Priority Data

Aug. 17, 2015 (EP) .................................. 15181226

(51) Int. Cl.
| G01N 33/48 | (2006.01) |
| A61B 34/10 | (2016.01) |
| A61B 34/00 | (2016.01) |
| A61B 34/20 | (2016.01) |

(52) U.S. Cl.
CPC ............. *A61B 34/10* (2016.02); *A61B 34/25* (2016.02); *A61B 2034/105* (2016.02); *A61B 2034/2048* (2016.02)

(58) Field of Classification Search
None
See application file for complete search history.

(56) References Cited

U.S. PATENT DOCUMENTS

| 9,058,647 | B2 | 6/2015 | Ishida et al. |
| 2004/0146191 | A1 | 7/2004 | Lu |
| 2009/0156930 | A1 | 6/2009 | Ein-Gal |
| 2011/0142308 | A1 | 6/2011 | Ishikawa et al. |
| 2011/0150310 | A1 | 6/2011 | Endo et al. |
| 2011/0262015 | A1* | 10/2011 | Ishikawa ............ G06K 9/6206 382/128 |
| 2011/0288415 | A1 | 11/2011 | Abe et al. |
| 2012/0114213 | A1 | 5/2012 | Buelow et al. |
| 2012/0157819 | A1 | 6/2012 | Jerebko et al. |
| 2013/0135312 | A1 | 5/2013 | Yang et al. |
| 2013/0187930 | A1* | 7/2013 | Millman ................ G06F 30/23 345/473 |
| 2014/0037161 | A1 | 2/2014 | Rucker et al. |
| 2015/0216496 | A1* | 8/2015 | Lee ........................ A61B 6/50 600/425 |
| 2015/0363971 | A1* | 12/2015 | Pan ......................... G06T 7/593 345/420 |
| 2016/0100821 | A1* | 4/2016 | Eggers .................. A61B 8/483 600/424 |
| 2016/0321384 | A1* | 11/2016 | Pal ........................ B33Y 50/02 |

FOREIGN PATENT DOCUMENTS

| CN | 102236913 A | 11/2011 |
| CN | 102473300 A | 5/2012 |
| CN | 102573650 A | 7/2012 |
| CN | 103251431 A | 8/2013 |
| DE | 103013213215 A1 | 1/2015 |
| JP | 2008289698 A | 5/2010 |
| WO | 2006055251 A2 | 5/2006 |
| WO | 2010058854 A1 | 5/2010 |
| WO | 2011007312 A1 | 1/2011 |
| WO | 2011052515 A1 | 5/2011 |
| WO | 2012137113 A1 | 10/2012 |
| WO | 2015108127 A1 | 7/2015 |

OTHER PUBLICATIONS

Eiben, B., et al. "Biomechanically guided prone to supine image registration of breast MRI using an estimated reference state." Biomedical Imaging (ISBI), 2013 IEEE 10th International Symposium on IEEE, 2013.

Eiben, B., et al. "Breast deformation modeling: comparison of methods to obtain a patient specific unloaded configuration." SPIE Medical Imaging. International Society for Optics and Photonics, 2014.

Rajagopal, V. et al., "Creating individual specific biomechanical models of the breast for medical image analysis", Academic Radiology, vol. 15, pp. 1425-1436, 2008, Abstract.

Vavourakis, V., et al. "Post breast conserving surgery finite element simulations of wound healing: A preliminary study towards cosmesis." 11th World Congress on Computational Mechanics, Jul. 20-25, 2014, Barcelona, Spain.

Ciechomski, P. et al., "Development and implementation of a Web-Enabled 3D consultation tol for breast augmentation surgery based on 3D-Image Reconstruction of 2D Pictures", Journal of Medical Internet Research. 2012; 14(1):e21.

Balaniuk, R. et al., "3D simulation of reconstructive breast surgery". Universidade Catolica de Brasilia, Brazil, Publication year 2006.

(Continued)

*Primary Examiner* — Anna Skibinsky (57) ABSTRACT

A system and a method are provided for simulating a breast deformation of a subject using sensor data obtained from an orientation sensor of a mobile device, with the orientation sensor being configured for sensing an orientation of the mobile device with respect to a direction of gravity. In accordance with the system and method, model data is accessed which defines a biomechanical model of a breast. A simulation subsystem is provided for obtaining the sensor data from the orientation sensor of the mobile device and for determining a gravitational breast deformation by applying a gravitational force to the biomechanical model in a direction which is defined based on the orientation of the mobile device. A deformed model may be displayed on a display of the mobile device. The system and the method provide an intuitive way of simulating the breast deformation.

14 Claims, 3 Drawing Sheets

(56) References Cited

OTHER PUBLICATIONS

Balaniuk, R. et al., "3D Dynamic simulation of the breast", Anais do VII Workshop de Informatica Medica (WIM2007), 2007.
Torres, R. et al., "Interactive deformation of heterogeneous volume data", URJC Madrid.

* cited by examiner

SIMULATING BREAST DEFORMATION

CROSS-REFERENCE TO PRIOR APPLICATIONS

This application is the U.S. National Phase application under 35 U.S.C. § 371 of International Application No. PCT/EP2016/069426, filed on Aug. 16, 2016, which claims the benefit of European Patent Application No. 15181226.0, filed on Aug. 17, 2015. These applications are hereby incorporated by reference herein.

FIELD OF THE INVENTION

The invention relates to a system for simulating a breast deformation of a subject. The invention further relates to a server and a mobile device comprising the system, and a computer program product comprising computer readable code embodied therein, the computer readable code being configured such that, on execution by a suitable computer or a processor, the computer or the processor is caused to perform the method.

BACKGROUND OF THE INVENTION

Planning a surgical intervention may assist a surgeon to predict a surgical outcome and account for necessary measures to be taken for a satisfactory outcome. Traditionally, surgical interventions performed on the breast, such as breast conserving surgery in breast cancer therapy, may be planned by the surgeon by, for example, drawing incision lines and tumor's location on the patient's skin. While traditional breast surgery planning is commonly done in an upright patient position, the surgeon has the possibility to change the patient's position, for example, from an upright position to a supine position, during the planning stage by simply moving the patient into a specific position. This enables the surgeon to consider shifts of incision lines induced, for example, by gravitational force. However, this traditional planning is not convenient and not sufficiently accurate, and image-based planning approaches are often preferred. Yet, even image-based planning approaches for predicting the outcome of, for example, breast conserving surgery in breast cancer therapy is often difficult for the surgeon and the patient. A reason may be that, depending on a positioning of the patient, a female breast may undergo relatively large scale deformations when loads such as gravitational forces are imparted to the breast tissue.

US 2009/0156930 A1 describes a method including obtaining reference image data-sets of a tissue related to respective reference patient tilt angles, wherein each reference image data-set is associated with a respective tilt angle, which is a combination of axial and transverse gravitational force components applied to the tissue, using the reference image data-sets to derive a formula relating an image data-set of said tissue to a given combination of axial and transverse gravitational force components, and using the formula to simulate an image data-set of a desired patient tilt angle.

A problem of US 2009/0156930 is that the method is limited in its options and is insufficiently intuitive to use.

SUMMARY OF THE INVENTION

It would be advantageous to obtain an improved system or method for simulating a breast deformation of a subject.

To better address this concern, a first aspect of the invention provides a system for simulating a breast deformation of a subject using sensor data obtained from an orientation sensor of a mobile device, the orientation sensor being configured for sensing an orientation of the mobile device with respect to a direction of gravity, the mobile device comprising a display, the system comprising:

an input interface for receiving model data, the model data defining a biomechanical model of a breast of the subject for enabling simulation of the breast deformation;

a simulation subsystem configured for:

obtaining the sensor data of the orientation sensor, the sensor data indicating the orientation of the mobile device;

determining, using the biomechanical model, a gravitational breast deformation by applying a gravitational force to the biomechanical model so as to obtain a deformed model; wherein the gravitational force is applied to the biomechanical model in a force direction which is defined based on the orientation of the mobile device; and generating output data for displaying the deformed model on the display.

The above measures involve providing an input interface for receiving model data which represents a biomechanical model of a breast of the subject for enabling a computer simulation of the breast deformation. A non-limiting example of the biomechanical model may be a geometrical model for use in computer simulations for simulating the breast mechanical behavior and physical interactions of the breast with its surrounding tissues and anatomical structures such as a chest of the subject. For example, the model data may comprise information relating to material characteristics of the breast tissue, and boundary conditions representing the breast interactions with the surrounding environment. The model data may be accessed from, for example, an internal or external storage.

The above measures further involve providing a simulation subsystem configured for obtaining sensor data of an orientation sensor of the mobile device. The sensor data indicates the orientation of the mobile device and may be obtained from, for example, an accelerometer, being an example of the orientation sensor. Orientation sensors are typically integrated into mobile devices. For example, accelerometers may be used which normally measure the gravitational force, also known as g-force, and which are known in the prior art per se, as well as their use for sensing an orientation of a device. It is, for example, known in the prior art per se to use accelerometers to align a screen of a device depending on the direction the device is held, for example, for switching between portrait and landscape modes. For example, single-axis and multi-axis types of accelerometer are available to detect magnitude and direction of proper acceleration as a vector quantity. Other types of orientation sensors also exist in the prior art per se and may also be used.

The simulation subsystem is further configured for applying a gravitational force to the biomechanical model in a direction which is defined based on the orientation of the mobile device as provided by the orientation sensor. The simulation subsystem may determine the deformation based on, for example, commonly available numerical methods for approximating solutions of mathematical differential equations, for example, equilibrium equations that govern a domain such as a biological tissue or an organ. The gravitational force may be applied to the biomechanical model as a body force. A body force is commonly defined as a force that acts throughout the volume of a body. To apply the gravitational force to the model as the body force, the orientation of the body force may be determined to account for the general orientation of the biomechanical model in the display of the mobile device. The general orientation of the biomechanical model may be linked to the orientation of the mobile device by, for example, a coordinate system of the biomechanical model being linked to a coordinate system of the display of the mobile device. As such, the orientation of the body force may be re-defined based on the orientation of the mobile device so as to simulate the direction of gravity when acting on the biomechanical model when displayed on the display of the mobile device.

The simulation subsystem is further configured for generating output data for displaying the deformed model on the display. The deformed model may show the breast when the gravitational force is applied to the model. It is noted, however, that the simulation subsystem may also be configured to generate data for displaying an un-deformed model. The inventors have realized that linking an orientation of the mobile device to an orientation of a gravitational force applied to a breast model may provide a user-friendly visualization framework for a surgeon and/or a patient and thus a highly intuitive way of simulating the breast deformation. Rather than having a pre-determined position of the subject, which has to be selected manually, the system according to the invention advantageously provides a "what you see is what you get" framework for breast simulation. Namely, instead of a limited number of pre-determined positions of the subject, any desired position of the subject can be intuitively considered and easily examined by adjusting the orientation of the mobile device. Such a framework makes the surgery planning easier. The surgeon may also readily carry the mobile device in a desired place and see/show and evaluate the gravitational breast deformation associated with a desired positioning of the patient. For example, the mobile device may be carried to a surgery room or a tele-conference room and the gravitational breast deformation associated with a supine or an upright positioning of the patient may be shown to the patient, to other surgeons or to trainee students. In particular, the mobile device may be brought into a sterile environment.

Optionally, the simulation subsystem is configured for re-determining the gravitational breast deformation when the sensor data indicates a change in the orientation of the mobile device with respect to the direction of gravity. Advantageously, the orientation of the mobile device may be adjusted such that an evaluation of the gravitational breast deformation associated with any desired positioning of the patient is obtainable. It is noted that the re-determining of the deformation may be performed in real-time. This may make the simulation more intuitive and user friendly.

Optionally, the system is provided with surgical plan data defining at least one geometrical element, the at least one geometrical element representing at least a part of a surgical plan and being linked to the biomechanical model, wherein the simulation subsystem is further configured for determining a deformation of the geometrical element when determining the gravitational breast deformation and for generating the output data for displaying the deformed geometrical element with the deformed model on the display. Advantageously, an outcome of a specific surgical planning, for example, an incision, in relation to the deformation of the breast may be visualized and evaluated quickly.

It is noted that a part of a surgical plan may be represented by a geometrical element. As a non-limiting example, the surgical plan may relate to a surgical intervention that comprises, for example, a cut on the breast or an excision of a portion of the breast. As such, the geometrical element may, for example, represent an incision line on the breast. The surgical plan data may thus define a location, a size and/or a direction of the incision line.

Optionally, the surgical plan data is provided as metadata to the model data. Advantageously, a user such as the surgeon may quickly use a pre-determined surgical plan, which is already defined by the surgical plan data.

Optionally, the at least one geometrical element comprises a line element representing an incision line in the surgical plan.

Optionally, the model data is obtained using at least one of a group of: magnetic resonance imaging, mammography, optical surface scanning, generic breast modeling, statistical breast modeling and ultrasound tomography.

Optionally, the biomechanical model comprises a mesh selected from a group of: a triangulated surface mesh, a surface mesh including a photo-realistic texture mapping and a volume mesh.

A further aspect of the invention provides a server comprising the system wherein the simulation subsystem is configured for receiving the sensor data from the mobile device, and for providing the output data to the mobile device. As such, the server and the mobile device may operate according to a client-server model.

A further aspect of the invention provides the mobile device comprising the system. As such, all functions of the system are integrated into the mobile device.

Optionally, the mobile device further comprises a user interaction subsystem comprising a user input interface and the display, wherein the surgical plan data defines a plurality of predefined surgical plans, and wherein the user interaction subsystem is configured for enabling a user to select the surgical plan from the plurality of predefined surgical plans. Advantageously, the user may evaluate multiple surgical plans and select a desired surgical plan based on, for example, a condition of the patient such as the weight of the patient or a breast size of the patient. As such, a surgeon may be able to choose between different surgical treatment options based on clinical or cosmetic criteria.

Optionally, the mobile device further comprises a user interaction subsystem comprising a user input interface and the display, wherein the user interaction subsystem is configured for enabling a user to draw the geometrical element on the displayed model. It may provide ample possibilities for the user to plan a patient-specific surgical intervention for each patient on the mobile device itself.

Optionally, the user interaction subsystem is configured to enable the user to edit the at least one geometrical element.

Optionally, the editing the at least one geometrical element comprises deleting the geometrical element and/or erasing and re-drawing a part of the at least one geometrical element. These editing options may advantageously make the simulation highly intuitive and user friendly.

A further aspect of the invention provides a method for simulating a breast deformation of a subject using sensor data obtained from an orientation sensor of a mobile device, the orientation sensor being configured for sensing an orientation of the mobile device with respect to a direction of gravity, the mobile device comprising a display, the method comprising:

receiving model data, the model data defining a biomechanical model of a breast of the subject for enabling simulation of the breast deformation;

obtaining the sensor data of the orientation sensor, the sensor data indicating the orientation of the mobile device;

determining, using the biomechanical model, a gravitational breast deformation by applying a gravitational force to the biomechanical model so as to obtain a model; wherein the gravitational force is applied to the biomechanical model in a force direction which is defined based on the orientation of the mobile device; and generating output data for displaying the deformed model on the display. In a further aspect of the invention, a computer program product is provided comprising computer readable code embodied therein, the computer readable code being configured such that, on execution by a suitable computer or processor, the computer or processor is caused to perform the method.

It will be appreciated by those skilled in the art that two or more of the above-mentioned embodiments, implementations, and/or aspects of the invention may be combined in any way deemed useful.

Modifications and variations of the server, the mobile device, the method, and/or the computer program product, which correspond to the described modifications and variations of the system, can be carried out by a person skilled in the art on the basis of the present description.

BRIEF DESCRIPTION OF THE DRAWINGS

These and other aspects of the invention are apparent from and will be elucidated with reference to the embodiments described hereinafter. In the drawings.

LIST OF REFERENCE NUMBERS

The following list of reference numbers is provided for facilitating the interpretation of the drawings and shall not be construed as limiting the claims.

| | |
|---|---|
| 10 | database |
| 12 | model data |
| 16, 26 | sensor data |
| 18, 28 | output data |
| 50, 200, 300, 400 | mobile device |

-continued

| | |
|---|---|
| 52, 240, 310, 410 | display |
| 100 | system for simulating a breast deformation |
| 110, 210 | input interface |
| 120, 220 | simulation subsystem |
| 230 | orientation sensor |
| 320, 370, 420, 470 | deformed biomechanical model |
| 430, 480 | geometrical element of a surgical plan |
| 500 | method for simulating a breast deformation |
| 510 | receiving model data |
| 520 | obtaining sensor data |
| 530 | determining a gravitational breast deformation |
| 540 | generating output data |
| 610 | a computer program product |
| 620 | a series of machine readable physical marks and/or elements having different electrical properties or values |

DETAILED DESCRIPTION OF EMBODIMENTS

Figure 1:
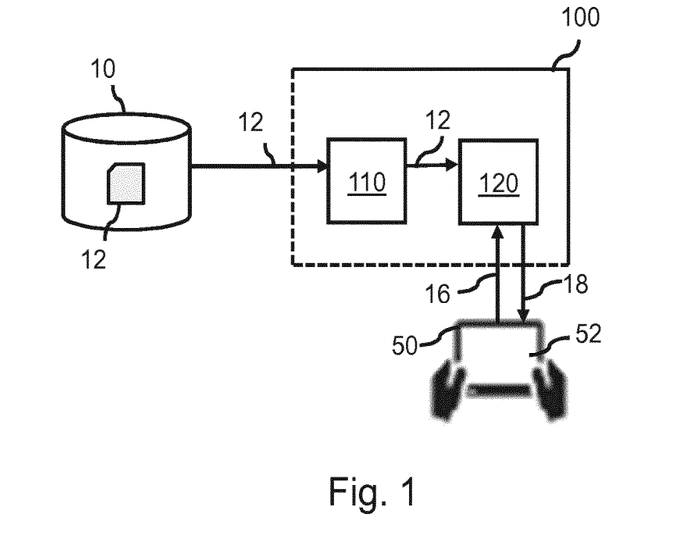
FIG. 1 shows a system for simulating a breast deformation of a subject using a mobile device.

FIG. 1 shows a system 100 for simulating a breast deformation of a subject using a mobile device 50, the mobile device 50 comprising a display 52 and an orientation sensor (not shown explicitly in FIG. 1) for sensing an orientation of the mobile device 50 with respect to a direction of gravity. It is noted that mobile devices comprising orientation sensors are known per se and include, for example, tablet devices, mobile phones, etc.

The system 100 comprises an input interface 110 for receiving model data 12, the model data 12 defining a biomechanical model of a breast of the subject for enabling simulation of the breast deformation. The model data 12 may be received from a database 10. Depending on the type of the database 10, the input interface 110 may take any suitable form, such as, but not limited to, an external memory or a storage interface, a network interface to local or wide area network, etc. It is noted that the database 10 may also be an internal database. Accordingly, the model data 12 may be accessed internally.

The model data 12 may have been generated using image data. The image data may represent shape information of the breast and/or information relating to a characteristic of a lesion, for example, shape information of the lesion. The image data may provide information of shape and/or composition of the breast. It is noted that the model data 12 may have been generated for a specific individual or a patient as the subject, or may have been generated based on an average of the shape of breasts of several subjects, for example, using statistical shape analysis methods. The model data 12 may also have been obtained and generated using other methods and from other sources, for example, but not limited to, from medical atlas data.

The system 100 further comprises a simulation subsystem 120. The simulation subsystem 120 is configured for obtaining sensor data 16 of the orientation sensor, the sensor data 16 indicating the orientation of the mobile device 50. The orientation sensor may be an accelerometer provided within the mobile device 50. There may be a software application running on the mobile device 50 which provides the sensor data 16 to the system 100. It is noted that, by way of example, the mobile device 50 may comprise a camera and may use an image analysis method to determine the orientations based on images obtained from the camera. The sensor data 16 may be directly or indirectly communicated from the mobile device 50 to the system 100 and the orientation sensor. For example, wireless communication may be used, such as, but not limited to, WiFi or BlueTooth®. It is noted that, although not explicitly shown in the Figures, the system 100 may comprise a separate sensor data interface for obtaining the sensor data 16 of the orientation sensor, with the sensor data interface being connected to the simulation subsystem. A non-limiting example is that the sensor data interface may be a WiFi or BlueTooth® wireless communications interface.

The simulation subsystem 120 is further configured for determining, using the biomechanical model, a gravitational breast deformation by applying a gravitational force to the biomechanical model so as to obtain a deformed model. The gravitational force is applied to the biomechanical model in a force direction which is defined based on the orientation of the mobile device 50. Gravity loading may be applied to the biomechanical model as a body force. To apply the gravitational force to the model, the orientation of the force may be determined based on a general orientation of the biomechanical model in the display 52 of the mobile device 50. The general orientation of the biomechanical model may be linked to the orientation of the mobile device 50 by, for example, but not limited to, linking a coordinate system of the model to a coordinate system of the mobile device 50. For example, a superior portion of the breast may point to an upper edge of the mobile device 50 while an inferior portion of the breast may point to a lower edge of the mobile device 50. As such, while the general orientation of the biomechanical model may remain fixed with respect to the mobile device coordinate system, the orientation of the applied gravitational force may be re-defined based on the orientation of the mobile device 50.

The simulation subsystem 120 may determine the deformation based on, for example, but not limited to, finite element or finite difference methods, which are generally known in the art per se. As an example, finite element methods, which are numerical methods for approximating solutions of mathematical differential equations may be used for solving equilibrium equations governing the breast. For example, Niftysim, which is an open source package, may be, used. Niftysim is total Lagrangian Explicit Dynamic Solver (TLED). This algorithm solves the basic equation of motion. Other known algorithms and packages such as ANSYS or ABAQUS or user-defined codes and programs may also be used in the simulation subsystem 120 for determining the deformation.

The simulation subsystem 120 is further configured for generating output data 18 for displaying the deformed model on the display 52. There may be a software application running on the mobile device 50 which receives the output data 18 from the system 100 and displays the deformed model on the display 52 of the mobile device 50. The output data 18 may be directly or indirectly communicated between the system 100 and the mobile device 50. For example, a wireless communication may be used. An example of output data 18 may be an image of the deformed model. Another example is a mesh representing the deformed model, which may be visualized by the mobile device 50. It is noted that, although not explicitly shown in the Figures, the system 100 may comprise a separate output data interface for providing the output data 18 to the display 52. A non-limiting example is that the output data interface may be a WiFi or BlueTooth® wireless communications interface.

It is noted that an un-deformed model may also be displayed on the display 52. To obtain the un-deformed model, the system 100 may be configured to un-load the biomechanical model, for example, by temporarily disregarding the sensor data 16, or by assuming no gravity or a default orientation.

The simulation subsystem 120 may be embodied by one or more microprocessors which execute appropriate software. The software may have been downloaded and/or stored in a corresponding memory, for example, but not limited to, a volatile memory such as RAM or a non-volatile memory such as Flash. It is noted that, in general, the simulation subsystem 120 of the system 100 may be implemented in the form of a circuit. Alternatively, one or more functional units of the system 100 may be implemented in the system 100 in the form of programmable logic, for example, but not limited to, a Field-Programmable Gate Array (FPGA). It is also noted that the system 100 may be implemented in a distributed manner, for example, but not limited to, involving different devices or apparatuses. For example, the distribution may be in accordance with a client-server model. FIG. 1 shows such a client-server model while FIG. 2 as described below shows an example where all features of the system 100 are integrated in a mobile device 200.

It is further noted that the biomechanical model may have been generated using known methods for generating computer models for simulating anatomical structures, for example, but not limited to, B. Eiben, et al. "Biomechanically guided prone-to-supine image registration of breast MRI using an estimated reference state." Biomedical Imaging (ISBI), 2013 IEEE 10th International Symposium on. IEEE, 2013, B. Eiben, et al. "Breast deformation modeling: comparison of methods to obtain a patient specific unloaded configuration." SPIE Medical Imaging. International Society for Optics and Photonics, 2014 or V. Rajagopal, A. Lee, J.-H. Chung, et al., Creating individual-specific biomechanical models of the breast for medical image analysis, Academic Radiology, vol. 15, pp. 1425-1436, 2008. As an example, in such methods, T2-weighted and fat-suppressed images of the breast may be combined to obtain a closed skin surface; noise reduction may be used with a bilateral filter; known segmentation methods may be used to segment the images into adipose and fibroglandular tissue and a chest wall so as to obtain the label images. From the label images, mesh models such as surface meshes may be generated using, for example, a marching cubes algorithm. The resulting mesh may be refined with, for example, a MeshLab's iso-parametrisation re-meshing module. The biomechanical model may be also generated based on volume mesh models, for example, tetrahedral volume mesh models. Volume mesh models may be generated using, for example, Tetgen. Each tissue in the model may have a pre-determined material property. Generic material properties may be assigned to the model. For example, compressible hyperelastic neo-Hookean constitutive material model with the strain energy-density function may be used. Boundary conditions may be defined for the biomechanical model. For example, it may be assumed that the breast tissues and muscle are firmly attached to the rib cage, thus a fixed-displacement boundary conditions may be applied at a posterior surface of the model.

Figure 2:
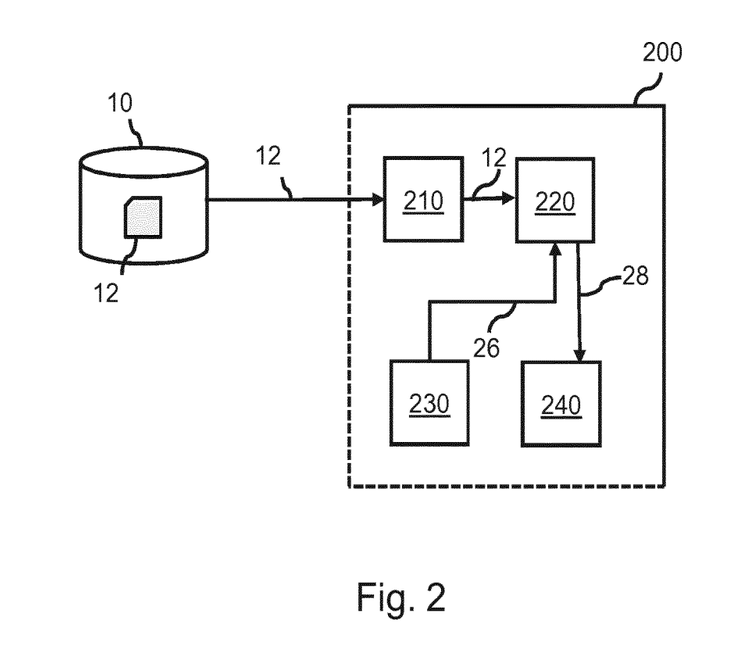
FIG. 2 shows a mobile device comprising a system for simulating a breast deformation of a subject.

FIG. 2 shows a mobile device 200 which comprises a system 100 for simulating a breast deformation of a subject. The mobile device 200 comprises an orientation sensor 230 and a display 240. The mobile device 200 further comprises an input interface 210 for receiving model data 12, the model data 12 defining a biomechanical model of a breast of the subject for enabling simulation of the breast deformation. The mobile device 200 further comprises a simulation subsystem 220. The simulation subsystem 220 is configured for obtaining sensor data 26 internally of the orientation sensor 230, the sensor data 26 indicating an orientation of the mobile device 200. The simulation subsystem 220 is further configured for determining, using the biomechanical model, a gravitational breast deformation by applying a gravitational force to the biomechanical model so as to obtain a deformed model; wherein the gravitational force is applied to the biomechanical model in a force direction which is defined based on the orientation of the mobile device 200. The simulation subsystem 220 is further configured for generating output data 28 for displaying the deformed model on the display 240. As such, compared to FIG. 1, the system in FIG. 2 is integrated into the mobile device 200 rather than being separated thereof.

It is noted that the simulation subsystem 120 of FIG. 1 and the simulation subsystem 220 of FIG. 2 may be configured for re-determining the gravitational breast deformation when the sensor data 16, 26 indicates a change in the orientation of the mobile device 50, 200 with respect to the direction of gravity. It is noted that the re-determining of the deformation may be performed in real-time, at fixed time intervals, etc.

Figure 3A:
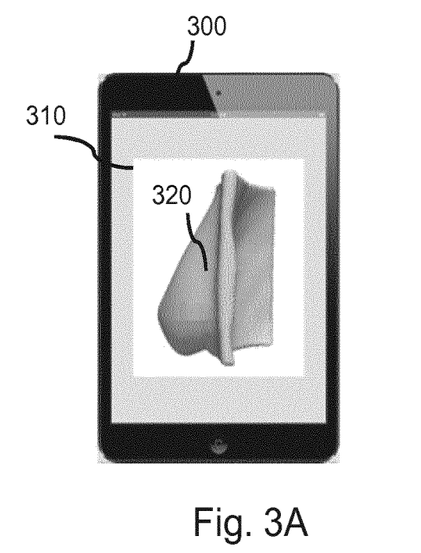
FIG. 3A shows a mobile device for simulating a breast deformation, the mobile device being in a particular orientation and a display of the mobile device displaying a deformed biomechanical model of the breast.

FIG. 3A shows a mobile device 300 for simulating a breast deformation, the mobile device 300 being in a certain orientation and a display 310 of the mobile device 300 displaying a deformed biomechanical model 320 of the breast.

Figure 3B:
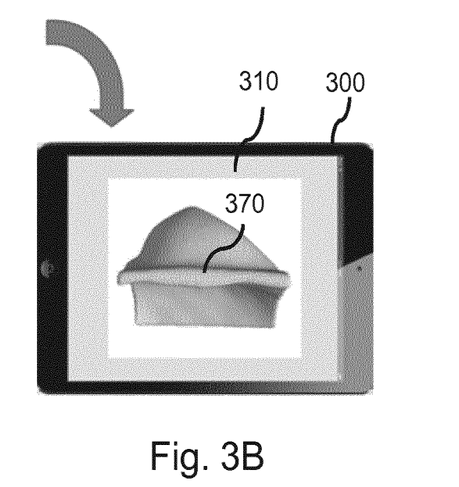
FIG. 3B shows the mobile device being rotated clockwise by 90 degrees, the display of the mobile device displaying a re-determined deformed model being calculated based on the rotated orientation of the mobile device.

FIG. 3B shows the mobile device 300 being rotated clockwise by 90 degrees, the display 310 of the mobile device 300 displaying a re-determined deformed model 370 being calculated based on a rotated orientation of the mobile device 300. In the example of FIG. 3B, the mobile device 300 is rotated by 90 degrees from an upright portrait orientation to a landscape orientation. It is noted that in the example of FIG. 3A and FIG. 3B, it is assumed that the gravitational force is in a perpendicularly downward direction with respect to the display 310 and as such, the biomechanical model 320 of FIG. 3A represents a breast in an upright position while the biomechanical model 370 of FIG. 3B represents a breast in a supine position.

Figure 4A:
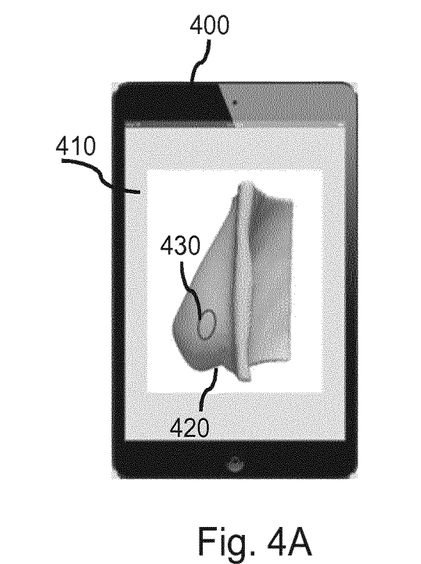
FIG. 4A shows a mobile device for simulating a breast deformation, the mobile device being in a particular direction and a display of the mobile device displaying a deformed biomechanical model of the breast and a geometrical element of a surgical plan.

FIG. 4A shows a mobile device 400 for simulating a breast deformation, the mobile device 400 being in a certain direction and a display 410 of the mobile device 400 displaying a deformed model 420 of the breast and a geometrical element 430 of a surgical plan. The geometrical element 430 is shown to be, by way of example, a circle representing an entry area in a surgical plan. The surgical plan may, for example, but not limited to, relate to a surgical intervention such as a cut on the breast or an excision of a portion of the breast. The surgical plan data may, for example, but not limited to, define a type of the surgical plan, a parameter of the surgical plan such as a size of a cut or a direction of the cut or a device used in the surgical intervention. Other geometrical elements representing different aspects of the surgical plan are equally conceivable.

Figure 4B:
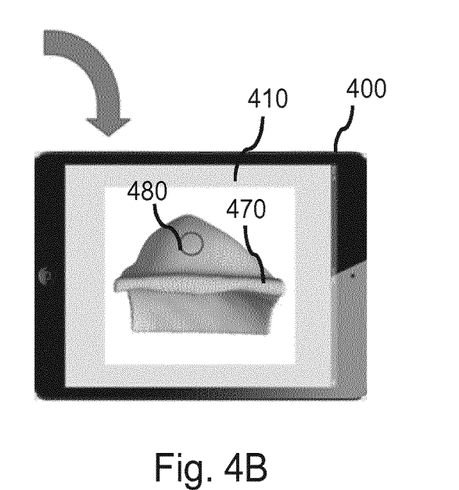
FIG. 4B shows the mobile device being rotated clockwise by 90 degrees, the display of the mobile device displaying a deformed geometrical element linked to a re-determined deformed model being calculated based on the rotated orientation of the mobile device.

FIG. 4B shows the mobile device 400 being rotated clockwise by 90 degrees, the display 410 of the mobile device 400 displaying a deformed geometrical element 480 linked to a re-determined deformed model 470 being calculated based on the rotated orientation of the mobile device 400. In the example of FIG. 4B, the mobile device 400 is rotated by 90 degrees from an upright portrait orientation to a landscape orientation.

FIG. 4B shows a rotated mobile device 400 comprising the system 100 of FIG. 1 for simulating a breast deformation, displaying a deformed model 470 of the breast and a deformed geometrical element 480 on the display 410 of the rotated mobile device 400.

It is noted that the mobile devices may comprise a user interaction subsystem (not explicitly shown in the figures) comprising a user input interface for enabling a user to select predefined surgical plans. The user interaction subsystem may be configured for enabling the user to draw a geometrical element on the displayed model. The user interaction subsystem may be configured to enable the user to at least edit the geometrical element. For example, the user interaction subsystem may be configured to enable the user to delete the geometrical element, erase and re-draw a part of the geometrical element and/or modify the geometrical element. The user interaction subsystem may comprise a user input interface for receiving user input data from a user device operable by the user. The user device may take various forms, including but not limited to, a touch screen, a key, a pen, a voice input, etc. The user interaction subsystem may be of a type which corresponds to the type of user device, i.e., it may be a thereto corresponding user device interface.

Figure 5:
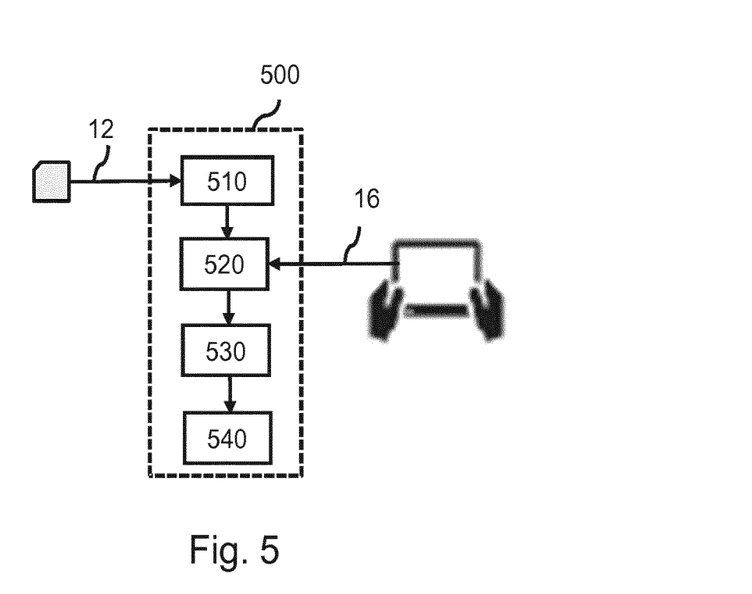
FIG. 5 shows a method for simulating a breast deformation of a subject.

FIG. 5 shows a method 500 for simulating a breast deformation of a subject using sensor data 16 obtained from an orientation sensor of a mobile device, with the orientation sensor being configured for sensing an orientation of the mobile device with respect to a direction of gravity, and the mobile device comprising a display. The method comprises, in an operation titled "RECEIVING MODEL DATA", receiving 510 model data 12, the model data 12 defining a biomechanical model of a breast of the subject for enabling simulation the breast deformation. The method 500 further comprises, in an operation titled "OBTAINING SENSOR DATA" obtaining 520 the sensor data 16 of the orientation sensor, the sensor data 16 indicating the orientation of the mobile device. The method 500 further comprises, in an operation titled "DETERMINING GRAVITATIONAL BREAST DEFORMATION", determining 530, using the biomechanical model, a gravitational breast deformation by applying a gravitational force to the biomechanical model so as to obtain a deformed model, wherein the gravitational force is applied to the biomechanical model in a force direction which is defined based on the orientation of the mobile device. The method 500 further comprises, in an operation titled "GENERATING OUTPUT DATA", generating 540 output data for displaying the deformed model on the display of the mobile device.

Figure 6:
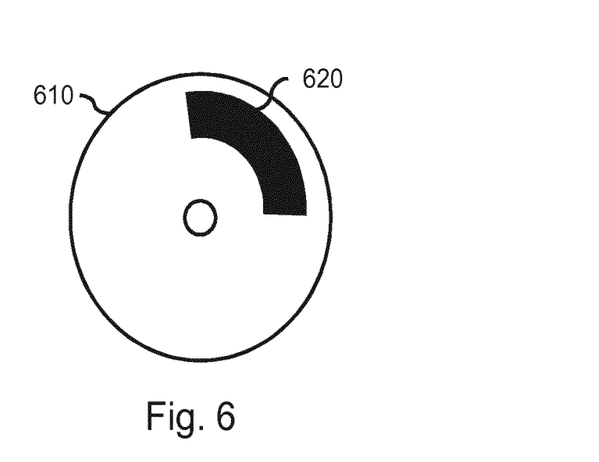
FIG. 6 shows a schematic representation of a computer program product comprising instructions for causing a processor system to perform the method for simulating a breast deformation of a subject.

The method 500 of FIG. 5 may be implemented on a computer as a computer implemented method, as dedicated hardware, or as a combination of both. As illustrated in FIG. 6, instructions for the computer, i.e., executable code, may be stored on a computer program product 610, for example, but not limited to, in the form of a series 620 of machine readable physical marks and/or as a series of elements having different electrical, for example, magnetic, or optical properties or values. The executable code may be stored in a transitory or a non-transitory manner. Examples of the computer program products include, but not limited to, a memory device, an optical storage device 610, an integrated circuit, a server, an online software, etc. FIG. 6 shows an optical disc.

It will be appreciated that, in accordance with the abstract of the present application, a system and a method are provided for simulating a breast deformation of a subject using sensor data obtained from an orientation sensor of a mobile device, with the orientation sensor being configured for sensing an orientation of the mobile device with respect to a direction of gravity. In accordance with the system and method, model data is accessed which defines a biomechanical model of a breast. A simulation subsystem is provided for obtaining the sensor data from the orientation sensor of the mobile device and for determining a gravitational breast deformation by applying a gravitational force to the biomechanical model in a direction which is defined based on the orientation of the mobile device. A deformed model may be displayed on a display of the mobile device. The system and the method provide an intuitive way of simulating the breast deformation.

Examples, embodiments or optional features, whether indicated as non-limiting or not, are not to be understood as limiting the invention as claimed.

It will be appreciated that the invention also applies to computer programs, particularly computer programs on or in a carrier, adapted to put the invention into practice. The program may be in the form of a source code, an object code, a code intermediate source and an object code such as in a partially compiled form, or in any other form suitable for use in the implementation of the method according to the invention. It will also be appreciated that such a program may have many different architectural designs. For example, a program code implementing the functionality of the method or the system according to the invention may be sub-divided into one or more sub-routines. Many different ways of distributing the functionality among these sub-routines will be apparent to the person skilled in art. The sub-routines may be stored together in one executable file to form a self-contained program. Such an executable file may comprise computer-executable instructions, for example, processor instructions and/or interpreter instructions (for example, Java interpreter instructions). Alternatively, one or more or all of the sub-routines may be stored in at least one external library file and linked with a main program either statically or dynamically, for example, at run-time. The main program contains at least one call to at least one of the sub-routines. The sub-routines may also comprise function calls to each other. An embodiment relating to the computer program product comprises computer-executable instructions corresponding to each processing stage of at least one of the methods set forth herein. These instructions may be sub-divided into sub-routines and/or stored in one or more files that may be linked statically or dynamically. Another embodiment relating to a computer program product comprises computer-executable instructions corresponding to each means of at least one of the systems and/or products set forth herein. These instructions may be sub-divided into sub-routines and/or stored in one or more files that may be linked statically or dynamically.

The carrier of the computer program may be any entity or a device capable of carrying the program. For example, the carrier may include a data storage, such as, but not limited to, a ROM, a CD ROM, a semiconductor ROM, or a magnetic recording medium, for example, a hard disk. Furthermore, the carrier may be a transmissible carrier such as, but not limited to, an electric or an optical signal, which may be conveyed via an electric or an optical cable, by a radio or other means. When the program is embodied in such a signal, the carrier may be constituted by such a cable or other device or means. Alternatively, the carrier may be an integrated circuit in which the program is embedded, the integrated circuit being adapted to perform, or used in the performance of the relevant method.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "comprise" and its conjugations does not exclude the presence of elements or stages other than those stated in a claim. The article "a" or "an" preceding an element does not exclude the presence of a plurality of such elements. The invention may be implemented by means of hardware comprising several distinct elements, and by means of a suitably programmed computer. In the device claim enumerating several means, several of these means may be embodied by one and the same item of hardware. The mere fact that certain measures are recited in mutually different dependent claims does not indicate that a combination of these measures cannot be used to advantage.

The invention claimed is:

1. A system for simulating a breast deformation of a subject, comprising:
    a hand-held mobile device comprising:
        a display;
        an orientation sensor configured to obtain sensor data indicating an orientation at which the hand-held mobile device is held;
        an input interface for receiving model data, wherein the model data defines a biomechanical model of a breast of the subject; and
        a processor configured to:
            receive the sensor data indicating the orientation at which the hand-held mobile device is held from the orientation sensor;
            generate a deformed model based on the biomechanical model and the orientation at which the hand-held mobile device is held; and
            output the deformed model to the display,
        wherein, to generate the deformed model, the processor is configured to:
            apply, to the biomechanical model, a first deformation comprising a simulated gravitational force in a first direction corresponding to the hand-held mobile device being held at a first orientation; and
            apply, to the biomechanical model, a different, second deformation comprising the simulated gravitational force in a different, second direction corresponding to the hand-held mobile device being held at a different, second orientation,
            wherein, for the first deformation and the second deformation, an orientation of the biomechanical model remains fixed with respect to the hand-held mobile device.

2. The system according to claim 1, wherein, to generate the deformed model, the processor is further configured to:
    determine that the sensor data indicates a change in the orientation at which the hand-held mobile device is held, wherein the change comprises an orientation change from the first orientation to the second orientation or an orientation change from the second orientation to the first orientation.

3. The system according to claim 1, wherein the system is provided with a surgical plan data defining at least one geometrical element, the at least one geometrical element representing at least a part of a surgical plan and being linked to the biomechanical model, wherein the processor is further configured to:
    determine a deformation of the geometrical element to generate the deformed model; and
    output the deformed geometrical element with the deformed model to the display such that the deformed geometrical element and the deformed model are shown with respect to the orientation at which the hand-held mobile device is held.

4. The system according to claim 3, wherein the surgical plan data is provided as metadata to the model data.

5. The system according to claim 3, wherein the at least one geometrical element comprises a line element representing an incision line in the surgical plan.

6. The system according to claim 1, wherein the model data is obtained using at least one of a group of: magnetic resonance imaging, mammography, optical surface scanning, generic breast modeling, statistical breast modeling and ultrasound tomography.

7. The system according claim 1, wherein the biomechanical model comprises a mesh selected from a group of: a triangulated surface mesh, a surface mesh including a photo-realistic texture mapping and a volume mesh.

8. The system according to claim 3, wherein the hand-held mobile device further comprises a user input interface, wherein the surgical plan data defines a plurality of pre-defined surgical plans, and wherein the processor is further configured to receive a selection of the surgical plan from the plurality of predefined surgical plans via the user input interface.

9. The system according to claim 3, wherein the hand-held mobile device further comprises a user input interface, wherein the processor is further configured to draw receive a designation of the at least one geometrical element on the displayed model via the user input interface.

10. The system according to claim 9, wherein the processor is further configured to receive an edit of the at least one geometrical element via the user input interface.

11. The system according to claim 10, wherein the edit of the at least one geometrical element comprises:
a deletion of the at least one geometrical element; or
a re-drawing of a part of the at least one geometrical element.

12. A method for simulating a breast deformation of a subject, comprising:
obtaining, using an orientation sensor of a hand-held mobile device, sensor data indicating an orientation at which the hand-held mobile device is held;
receiving model data at an input interface of the hand-held mobile device, wherein the model data defines a biomechanical model of a breast of the subject;
generating, using a processor of the hand-held mobile device, a deformed model based on the biomechanical model and the orientation at which the hand-held mobile device is held, wherein the generating the deformed model comprises:
applying, to the biomechanical model, a first deformation comprising a simulated gravitational force in a first direction corresponding to the hand-held mobile device being held at a first orientation; and
applying, to the biomechanical model, a different, second deformation comprising the simulated gravitational force in a different, second direction corresponding to the hand-held mobile device being held at a different, second orientation,
wherein, for the first deformation and the second deformation, an orientation of the biomechanical model remains fixed with respect to the hand-held mobile device; and
outputting the deformed model to a display of the hand-held mobile device.

13. A non-transitory computer program product comprising a computer readable medium comprising computer readable code embodied therein, the computer readable code being configured such that, on execution by a suitable computer or a processor, the computer or the processor is caused to perform the method of claim 12.

14. The system according to claim 1, further comprising a server, wherein the input interface is configured to receive the model data via the server.

* * * * *